(12) United States Patent
Herscovici-Cohen et al.

(10) Patent No.: US 10,354,135 B2
(45) Date of Patent: Jul. 16, 2019

(54) NON INVASIVE METHOD AND APPARATUS FOR DETERMINING LIGHT-SLEEP AND DEEP-SLEEP STAGES

(75) Inventors: Sarah Herscovici-Cohen, Zikhron-Yaakov (IL); Jacob Sheffy, Haifa (IL)

(73) Assignee: Itamar Medical Ltd., Caesarea (IL)

( * ) Notice: Subject to any disclaimer, the term of this patent is extended or adjusted under 35 U.S.C. 154(b) by 479 days.

(21) Appl. No.: 12/937,737

(22) PCT Filed: Apr. 13, 2009

(86) PCT No.: PCT/IB2009/051535
§ 371 (c)(1),
(2), (4) Date: Oct. 14, 2010

(87) PCT Pub. No.: WO2009/144598
PCT Pub. Date: Dec. 3, 2009

(65) Prior Publication Data
US 2011/0092831 A1    Apr. 21, 2011

Related U.S. Application Data

(60) Provisional application No. 61/071,127, filed on Apr. 14, 2008.

(51) Int. Cl.
*A61B 5/00* (2006.01)
*G06K 9/00* (2006.01)
(Continued)

(52) U.S. Cl.
CPC ............ *G06K 9/0053* (2013.01); *A61B 5/024* (2013.01); *A61B 5/1073* (2013.01); *A61B 5/4812* (2013.01)

(58) Field of Classification Search
USPC ........................................................ 600/500
See application file for complete search history.

(56) References Cited

U.S. PATENT DOCUMENTS

2003/0004423 A1   1/2003  Lavie et al.
2005/0080349 A1   4/2005  Okada et al.
(Continued)

FOREIGN PATENT DOCUMENTS

CN            1430484        7/2003
CN            1676094       10/2005
WO     WO 2004/026133        4/2004

OTHER PUBLICATIONS

Herscovici et al., Detecting REM sleep from the finger: automatic REM sleep algorithm based on peripheral arterial tone (PAT) and actigraphy, 2006, Physiological Measurement, 27, pp. 1-12.*
(Continued)

*Primary Examiner* — Michael R Bloch

(57) ABSTRACT

A method and apparatus for detecting and distinguishing epochs of deep-sleep from epochs of light-sleep of a subject by sensing by a peripheral pulse signal related to the systemic circulation of the subject, preferably a peripheral arterial tone (PAT) sensor for sensing pulsatile arterial volume changes in a digit (e.g., a finger) of the subject reflecting sympathetic tone variations; analyzing the sensed pulse signals for determining therefrom a number of features, particularly seven specific variables in each of two time periods; and utilizing the results of the analysis for determining whether the epoch detected is a light-sleep epoch or a deep-sleep epoch.

31 Claims, 8 Drawing Sheets

(51) Int. Cl.
A61B 5/024 (2006.01)
A61B 5/107 (2006.01)

(56) References Cited

U.S. PATENT DOCUMENTS

2005/0177051 A1 8/2005 Almen
2005/0234314 A1* 10/2005 Suzuki et al. ............... 600/301
2007/0118026 A1 5/2007 Kameyama et al.

OTHER PUBLICATIONS

Herscovici et al., Detecting REM sleep from the finger: automatic REM sleep algorithm based on peripheral arterial tone (PAT) and actigraphy, 2007, Physiological Measurement, 28, pp. 129-140.*
Translation of Office Action dated Feb. 7, 2013 From the State Intellectual Property Office of the People's Republic of China Re. Application No. 200980122295.7.
Translation of Office Action dated Mar. 1, 2013 From the ROSPATENT, Federal Government Institution, Federal Institute of Industrial Property of the Federal Service for Intellectual Property, Patents and Trademarks Re. Application No. 2010146145.
Communication pursuant to Rules 70(2) and 70a(2) EPC dated Jun. 11, 2013 From the European Patent Office Re. Application No. 09754225.2.
Supplementary European Search Report and the European Search Opinion dated May 24, 2013 From the European Patent Office Re. Application No. 09754225.2.
Translation of Office Action dated Jun. 4, 2012 From the State Intellectual Property Office of the People's Republic of China Re. Application No. 200980122295.7.
Jiang et al. "R-R Intervals Analysis and Sleep Scoring", Journal of Biomedical Engineering Research, 22(3): 17-20, 2003.
International Search Report and the Written Opinion dated Sep. 30, 2009 From the International Searching Authority Re.: Application No. PCT/IB09/51535.
Clifford "Signal Processing Methods for Heart Rate Variability", Thesis in Fulfilment of the Requirements for the Degree of Doctor of Philosphy, Department of Engineering Science, University of Oxford, St. Cross College, UK, p. 244, 2002.
International Preliminary Report on Patentability dated Oct. 28, 2010 From International Bureau of WIPO Re. Application. No. PCT/IB2009/051535.
Communication Pursuant to Article 94(3) EPC dated Jan. 17, 2014 From the European Patent Office Re. Application No. 09754225.2.
Office Action dated Oct. 18, 2013 From the State Intellectual Property Office of the People's Republic of China Re. Application No. 200980122295.7 and Its Translation Into English.
Search Report dated Oct. 18, 2013 From the State Intellectual Property Office of the People's Republic of China Re. Application No. 200980122295.7 and Its Translation Into English.
Aydin et al. "Cardiac Autonomic Activity in Obstructive Sleep Apnea. Time-Dependent and Spectral Analysis of Heart Rate Variability Using 24-Hour Holter Electrocardiograms", Texas Heart Institute Journal, 31(2): 132-136, 2004.
Bar et al. "Evaluation of A Portable Device Based on Peripheral Arterial Tone for Unattended Home Sleep Studies", Chest, 123(3): 695-703, Mar. 2003.
Berlad et al. "Power Spectrum Analysis and Heart Rate Variability in Stage 4 and REM Sleep: Evidence for State-Specific Changes in Autonomic Dominance", Journal of Sleep Research, 2(2): 88-90, Jun. 1993.
Bonnet et al. "Heart Rate Variability: Sleep Stage, Time of Night, and Arousal Influences", Electroencephalography and Clinical Neurophysiology, 102: 390-396, 1997.
Brandenberger et al. "Sleep Stage 2: An Electroencephalographic, Autonomic, and Hormonal Duality", Sleep, 28(12): 1535-1540, 2005.
Brooks et al. "Baroreflex Control of Heart Rate in A Canine Model of Obstructive Sleep Apnea", American Journal of Respiratory and Critical Care Medicine, 159: 1293-1297, 1999.
Burgess et al. "Cardiac Autonomic Nervous System Activity During Presleep Wakefulness and Stage 2 NREM Sleep", Journal of Sleep Research, 8: 113-122, 1999.
Burgess et al. "Estimating Cardiac Autonomic Activity During Sleep: Impedance Cardiography, Spectral Analysis, and Poincare Plots", Clinical Neurophysiology, 115: 19-28, 2004.
Busek et al. "Spectral Analysis of Heart Rate Variability in Sleep", Physiological Research, 54: 369-376, 2005.
Chesson et al. "Practice Parameters for the Use of Portable Monitoring Devices in the Investigation of Suspected Obstructive Sleep Apnea in Adults", Sleep, 26(7): 907-913, 2003.
Dvir et al. "Evidence for Fractal Correlation Properties in Variations of Peripheral Arterial Tone During REM Sleep", American Journal of Physiology, Heart and Circulatory Physiology, 283(1): H434-H439, Jul. 2002.
Elsenbruch et al. "Heart Rate Variability During Waking and Sleep in Healthy Males and Females", Sleep, 22(8): 1067-1071, 1999.
Ferri et al. "Cyclic Alternating Pattern and Spectral Analysis of Heart Rate Variability During Normal Sleep", Journal of Sleep Research, 9 13-18. 2000.
Futuro-Neto et al. "Changes in Sympathetic Activity to Heart and Blood Vessels During Desynchronized Sleep", Brain Research, 252: 259-268, 1982.
Hedner et al. "A Novel Adaptive Wrist Actigraphy Algorithm for Sleep-Wake Assessment in Sleep Apnea Patients", Sleep, 27(8): 1560-1566, 2004.
Hornyak et al. "Sympathetic Muscle Nerve Activity During Sleep in Man", Brain, 114: 1281-1295, 1991.
Jo et al. "Determinants of Heart Rate Variability in Obstructive Sleep Apnea Syndrome During Wakefulness and Sleep", American Journal of Physiology, Heart and Circulatory Physiology, 288: H1103-H1112, 2005.
Kirby et al. "Differential Effects of Sleep Stage on Coronary Hemodynamic Function", The American Journal of Physiology, 256(5/Pt.2): H1378-H1383, May 1989.
Kodama et al. "Attenuation of Regional Differentiation of Sympathetic Nerve Activity During Sleep in Humans", Journal of the Autonomic Nervous System, 74: 126-133, 1998.
Lavie et al. "Peripheral Vasoconstriction During REM Sleep Detected by A New Plethysmographic Method", Nature Medicine, 6(6): 606, Jun. 2000.
Levy et al. "Sleep Fragmentation: Clinical Usefulness of Automatic Markers", Sleep Medicine, 4: 489-491, 2003.
Liguori et al. "Sleep Stage-Related Changes in Sympathetic Sudomotor and Vasomotor Skin Responses in Man", Clinical Neurophysiology, 111: 434-439, 2000.
Margel et al. "Long-Term Intermittent Exposure to High Ambient $CO_2$ Causes Respiratory Disturbances During Sleep in Submariners", Chest, 124: 1716-1723, 2003.
Monti et al. "Autonomic Control of the Cardiovascular System During Sleep in Normal Subjects", European Journal of Applied Physiology, 87(2): 174-181, Apr. 26, 2002.
Narkiewicz et al. "Altered Cardiovascular Variability in Obstructive Sleep Apnea", Circulation, 98(11): 1071-1077, Sep. 15, 1998.
Narkiewicz et al. "Sympathetic Activity in Obese Subjects With and Without Obstructive Sleep Apnea", 98(8): 772-776, Aug. 25, 1998.
Noll et al. "Skin Sympathetic Nerve Activity and Effector Function During Sleep in Humans", Acta Physiologica Scandinavica, 151(3): 319-329, Jul. 1994.
Okada et al. "Changes in Muscle Sympathetic Nerve Activity During Sleep in Humans", Neurology, 41: 1961-1966, Dec. 1, 1991.
Penzel et al. "Ambulatory Recording of Sleep Apnea Using Peripheral Arterial Tonometry", Proceedings of the 26th Annual International Conference of the IEEE EMBS, San Francisco, CA, USA, Sep. 1-5, 2004, p. 3856-3859, Sep. 2004.
Penzel et al. "Comparison of Detrended Fluctuation Analysis and Spectral Analysis for Heart Rate Variability in Sleep and Slee Apnea", IEEE Transactions on Biomedical Engineering, 50(10): 1143-1151, Oct. 2003.

(56) References Cited

OTHER PUBLICATIONS

Penzel et al. "Heart Rate Variability During Sleep Stages in Normal and in Patients With Sleep Apnea", Medical Infobahn for Europe, Proceedings of MIE2000 and GMDS2000, 77: 1256-1260, 2000.
Penzel et al. "Peripheral Arterial Tonometry, Oximetry and Actigraphy for Ambulatory Recording of Sleep Apnea", Physiological Measurement, 25: 1025-1036, 2004.
Pillar et al. "Upper Airway Muscle Responsiveness to Rising P[CO2] During NREM Sleep", Journal of Applied Physiology, 89(4): 1275-1282, Oct. 1, 2000.
Pressman et al. "Relationship of Autonomic Nervous System Activity to Daytime Sleepiness and Prior Sleep", Sleep, 12(3): 239-245, 1989.
Silber et al. "The Visual Scoring of Sleep in Adults", Journal of Clinical Sleep Medicine, JCSM, 3(2): 121-131, 2007.
Somers et al. "Sympathetic-Nerve Activity During Sleep in Normal Subjects", The New England Journal of Medicine, 328(5): 303-307, Feb. 4, 1993.
Svetnik et al. "Evaluation of Automated and Semi-Automated Scoring of Polysomnographic Recordings From A Clinical Trial Using Zolpidem in the Treatment of Insomnia", Sleep, 30(11): 1562-1574, 2007.
Takeuchi et al. "Sleep-Related Changes in Human Muscle and Skin Sympathetic Nerve Activities", Journal of the Autonomic Nervous System, 47: 121-129, 1994.
Trinder et al. "Autonomic Activity During Human Sleep as A Function of Time and Sleep Stage", Journal of Sleep Research, 10: 253-264, 2001.
Villa et al. "Effects of Sleep Stage and Age on Short-Term Heart Rate Variability During Sleep in Healthy Infants and Children", Chest, 117: 460-466, 2000.
Virtanen et al. "Sleep Stage Dependent Patterns of Nonlinear Heart Rate Dynamics in Postmenopausal Women", Autonomic Neuroscience: Basic and Clinical, 134: 74-80, 2007.
Ward Flemons et al. "Home Diagnosis of Sleep Apnea: A Systemic Review of the Literature. An Evidence Review Cosponsored by the American Academy of Sleep Medicine, the American College of Chest Physicians, and the American Thoracic Society", Chest, 124(4): 1543-1579, Oct. 2003.
Notification of the Results of the Examination on Patentability dated Mar. 21, 2014 From the Federal Government Institution, Federal Institute of Industrial Property of the Federal Service for Intellectual Property, Patents and Trademarks of the Russian Federation Re. Application No. 2010146145 and Its Translation Into English.
Requisition by the Examiner dated Oct. 20, 2015 From the Canadian Intellectual Property Office Re. Application No. 2,721,154.
Examination Report Under Sections 12 & 13 of the Patents Act, 1970 and the Patents Rules, 2003 dated Feb. 23, 2018 From the Government of India, Intellectual Property India, Patents, Designs, Trade Marks, Geographical Indications Re. Application No. 2404/MUMNP/2010. (5 Pages).

\* cited by examiner

NON INVASIVE METHOD AND APPARATUS FOR DETERMINING LIGHT-SLEEP AND DEEP-SLEEP STAGES

RELATED APPLICATION

This Application is a National Phase of PCT Patent Application No. PCT/IB2009/051535 having International filing date of Apr. 13, 2009, which claims the benefit of U.S. Provisional Patent Application No. 61/071,127 filed on Apr. 14, 2008. The contents of the above Applications are all incorporated herein by reference.

FIELD AND BACKGROUND OF THE INVENTION

The present invention relates to a method and apparatus for non-invasively determining light-sleep and deep-sleep stages by sensing peripheral pulse signals related to the systemic circulation of the subject. The invention is particularly useful when utilizing a peripheral arterial tone (PAT) sensor, such as disclosed in U.S. patent application Ser. No. 10/195,464, filed Jul. 16, 2002, U.S. patent application Ser. No. 10/471,580, filed Sep. 12, 2003, and U.S. patent application Ser. No. 10/520,273, filed Jan. 18, 2005, all assigned to the same assignee as the present application, the descriptions of which are incorporated herein by reference, and the invention is therefore described below with respect to such sensors.

To facilitate understanding the following description, there are set forth below the meanings of a number of acronyms frequently used therein.
REM rapid eye movement (sleep stage)
NREM non-rapid eye movement (sleep stage)
PAT peripheral arterial tone (signal)
AMP PAT signal amplitude
EEG electroencephalogram—electrical currents associated with the brain
EMG electromyogram—electrical currents associated with muscles
EOG electrooculography—measuring the resting potential of the retina
ANS automatic nervous system
OSA obstructive sleep apnea
OSAS obstructive sleep apnea syndrome
RDI respiratory disturbance index
PSG Polysomnography
IPP inter-pulse period (heart-rate)
DFA detrended fluctuation analysis
VLF peak of the very low frequency spectral density
LF peak of the low frequency spectral density
ULF peak of the ultra-low frequency spectral density
HF peak of the high frequency spectral density
Spec Ratio of LF to HF
NF neighboring filter
ROC Receiver Operating Characteristic (curve)
AASM American Academy of Sleep Medicine Detecting various sleep-state conditions, particularly sleep-wake status and REM sleep stages versus NREM sleep stages, is commonly used in the determination of various medical conditions, particularly obstructive sleep conditions such as OSA, and REM related apnea. At the present time, detecting the various sleep-state conditions is commonly done by PSG in a sleep laboratory equipped with specialized instruments for sensing various conditions, particularly the EEG signal, and utilizing the results of the sensed conditions for determining the sleep state. The above-cited U.S. patent application Ser. No. 10/195,464 filed Jul. 16, 2002 utilizes an external probe applied to peripheral body location, such as a digit (finger or toe) of the individual, for detecting peripheral pulse signals related to the systemic circulation of the subject. The preferred embodiment therein disclosed utilizes a PAT probe for detecting changes in the peripheral vascular bed volume of the subject. Likewise, the above-cited U.S. patent application Ser. No. 10/520,273, filed Jan. 18, 2005, utilizes an external probe capable of being applied at virtually any body site of the individual, for detecting peripheral pulse signals related to the systemic circulation of the subject.

The present invention is directed particularly to detecting and distinguishing epochs of deep-sleep from epochs of light-sleep using a probe applied to the individual for sensing peripheral pulse signals related to the systemic circulation of the subject, which can be used for unattended ambulatory sleep monitoring, not requiring the sensors (e.g., EEG sensors) or other specialized instruments provided in a sleep laboratory.

The invention is particularly effective when using a PAT probe described in the above-cited U.S. application Ser. Nos. 10/195,464, 10/471,580, and 10/520,273, for detecting changes in the peripheral vascular bed volume of the individual, and is therefore described below particularly with respect to the use of such sensors. For the sake of brevity, the construction and operation of such PAT sensors are not described herein, but are available in the above-cited U.S. application Ser. Nos. 10/195,464, 10/471,580, and 10/520,273, incorporated herein by reference for this purpose. While the invention preferably uses such a PAT sensor, it will be appreciated that the invention could use other sensors for sensing peripheral pulse signals. A number of such other sensors are well known to the art. These include, but are not restricted to; skin optical density or skin surface-reflectivity devices, optical plethysmographs, (also known as photo-plethysmograps), Doppler ultrasound devices, laser Doppler device, pulse oximeters, segmental plethysmographs, circumferential strain gauge devices, isotope washout techniques, thermal washout techniques, electromagnetic techniques, Hall effect sensors, and the like for sensing peripheral pulse signal related to the systemic circulation of the subject.

Non-Rapid Eye Movement (NREM) sleep was traditionally classified into four stages, where stage 1 was defined as drowsiness (just falling asleep); stage 2 as light-sleep, and stages 3 and 4 as deep sleep, which is considered the more refreshing sleep. Both Stages 1 and 2 NREM sleep, classified as light-sleep, are characterized by theta EEG activity. In stage 1 NREM sleep, there may be slow vertical eye rolling while stage 2 of NREM sleep is characterized by sleep spindles and/or K complexes, no eye movements and reduced EMG activity. Stages 3 and 4 NREM sleep, classified as deep sleep, are characterized by delta EEG activity (which is the reason for the common term describing these stages as slow-wave sleep), no eye movements (although the EOG channels commonly show EEG artifacts), and even further diminished EMG activity (Lavie et al., 2002; Rechtschaffen and Kales, 1968). Given the more restorative nature of deep sleep, and the common findings of increased deep sleep following sleep deprivation or treatment for sleep disorders, it is of substantial clinical importance to distinguish between light-sleep and deep-sleep stages.

Recently, the AASM Visual Scoring Task Force re-examined these rules and came up with a new terminology for sleep stages. Since no evidence was found to justify dividing slow wave sleep into two stages, i.e. stages 3 and 4 of NREM sleep, it was proposed to combine these into a single stage of deep sleep (Silber et al., 2007) However, despite coming up with new scoring criteria, as with its predecessor (Rechtschaffen & Kales, 1968) the activity of the autonomic nervous system (ANS) still does not play a major role in scoring sleep stages, despite increasing evidence for substantial and differential activities of this system in the various sleep stages. In other words, regardless of the EEG changes measured via surface electrodes, light and deep sleep seem to differ by autonomic activations manifested predominantly as higher and more stable parasympathetic activity in deep sleep than light NREM sleep (Dvir et al., 2002; Herscovici et al., 2007; Lavie et al., 2000; Narkiewicz et al., 1998; Penzel et al., 2000; Penzel et al., 2003; Penzel et al., 2004; Pressman and Fry, 1989; Villa et al., 2000; Virtanen et al., 2007). Thus, ANS such as heart rate, heart rate variability or peripheral arterial tone may be of significant importance in evaluating the quality of NREM sleep.

The Watch-PAT 100 (WP100 or WP200 further version of the same system) is an ambulatory sleep recorder, which is based predominantly on recordings of the peripheral arterial tone (PAT) signal and pulse rate (two important outputs of the autonomic nervous system), actigraphy and pulse oximetry (Bar et al, 2004, Penzel et al, 2004, Pillar et al 2003). It has been shown to accurately detect sleep vs. wakefulness (Hedner et al., 2004), as well as to detect REM sleep (Dvir et al., 2002; Herscovici et al., 2007; Lavie et al., 2000). Given the well established changes of the autonomic nervous system characteristics in patients with obstructive sleep apnea (Aydin et al., 2004; Brooks et al., 1999; Jo et al., 2005; Narkiewicz et al., 1998; Narkiewicz and Somers, 1997; Penzel et al., 2000; Penzel et al., 2003; Pepin et al., 1994), the WP100 has been tested on both normal subjects and patients with OSA (Bar et al., 2003; Dvir et al., 2002; Hedner et al., 2004; Herscovici et al., 2007; Lavie et al., 2000; Penzel et al., 2004; Pillar et al., 2003). However, the ability to distinguish between light-sleep and deep sleep based on autonomic nervous system (ANS) outputs monitored by the WP100 has not been examined.

Deep sleep has been shown to be associated with increased parasympathetic activity (projected in heart rate and heart rate variability), and more regular and stable heart rate (Berlad et al., 1993; Bonnet and Arand, 1997; Brandenberger et al., 2005; Burgess et al., 1999; Busek et al., 2005; Elsenbruch et al., 1999; Ferri et al., 2000; Kirby and Verrier, 1989; Kodama et al., 1998; Liguori et al., 2000; Monti et al., 2002; Negoescu and Csiki, 1989; Noll et al., 1994; Okada et al., 1991; Penzel et al., 2003; Pressman and Fry, 1989; Somers et al., 1993; Takeuchi et al., 1994; Trinder et al., 2001; Villa et al., 2000). Therefore it would be highly desirable to develop an algorithm which will allow detecting and distinguishing light from deep sleep solely based on a sensor for sensing a peripheral pulse signal related to the systemic circulation of a subject. A PAT probe is particularly useful for the this purpose since the vascular tone and the pulse rate both are channels of the PAT probe in the WP100. This would allow for testing the hypothesis that autonomic nervous system output changes are sleep-stage dependent. As mentioned, other sensors for sensing peripheral pulse signals could be used to this end.

OBJECTS AND BRIEF SUMMARY OF THE PRESENT INVENTION

An object of the present invention is to provide a method, and also apparatus, for detecting and distinguishing epochs of deep-sleep from epochs of light-sleep which could be used for unattended ambulatory sleep monitoring of a subject outside of a sleep laboratory and not requiring the special equipment, such as an EEG sensor, usually available only in sleep laboratories.

According to a broad aspect of the present invention, there is provided a method of detecting and distinguishing epochs of deep sleep from epochs of light-sleep of a subject, comprising: (a) sensing from the subject, for the period of the epoch, a peripheral pulse signal related to the systemic circulation of the subject; (b) analyzing the sensed peripheral pulse signal for determining therefrom one or more variables that are derived from the following features where each feature can provide 2 variables—one is an amplitude variable and the other is a heart rate variable (altogether up to 14 variables): (1) the mean amplitude and heart rate of the sensed peripheral pulse signal; (2) a scaling coefficient of a detrended fluctuation analysis (DFA) of the amplitude and heart-rate of the sensed peripheral pulse signal; (3) the peak of the low frequency spectral density (LF) of the amplitude and heart rate of the sensed peripheral pulse signal; (4) the peak of the very-low frequency spectral density (VLF) of the amplitude and heart rate of the sensed peripheral pulse signal, (5) the peak of the ultra-low frequency spectral density (ULF) of the amplitude and heart rate of the sensed peripheral pulse signal; (6) the peak of the high frequency spectral density (HF) of the amplitude and heart rate of the sensed peripheral pulse signal; and (7) the ratio of LF to HF (Spectral Ratio) of the amplitude and heart rate; and (c) utilizing the result of the foregoing analysis to determine whether the epoch detected is a light-sleep epoch or a deep-sleep epoch.

In the preferred embodiment of the invention described below, all the above variables determined by the analyzing operation are utilized to determine whether the epoch detected is a light-sleep or deep-sleep epoch. Also in that embodiment, the sensed peripheral pulse signals are sensed by a PAT sensor applied to a digit of the subject.

Further, in the described preferred embodiment, there are a plurality of the epochs each of a period of seconds within a sliding window of minutes. The peripheral pulse signal is sensed from the subject during each of two time periods. Each peripheral pulse signal is analyzed as set forth in operation (b) for each time period, and the results of such analyses are utilized to determine whether each epoch is a light-sleep epoch or a deep-sleep epoch.

According to a further aspect of the present invention, there is provided apparatus for detecting and distinguishing epochs of deep sleep from epochs of light-sleep of a subject, comprising: (a) a sensor for sensing from the subject, for the period of the epoch, a peripheral pulse signal related to the systemic circulation of the subject;

(b) a processor for analyzing the sensed peripheral pulse signal for determining therefrom one or more variables that are derived from the following features where each feature can provide 2 variables—one is an amplitude variable and the other is a heart rate variable (altogether up to 14 variables): (1) the mean amplitude and heart rate of the sensed peripheral pulse signal or the (2) a scaling coefficient of a detrended fluctuation analysis (DFA) of the amplitude and heart-rate of the sensed peripheral pulse signal; (3) the peak of the low frequency spectral density (LF) of the amplitude and heart rate of the sensed peripheral pulse signal; (4) the peak of the very-low frequency spectral density (VLF) of the amplitude and heart rate of the sensed peripheral pulse signal, (5) the peak of the ultra-low frequency spectral density (ULF) of the amplitude and heart rate of the sensed peripheral pulse signal; (6) the peak of the high frequency spectral density (HF) of the amplitude and heart rate of the sensed peripheral pulse signal; and (7) the ratio of LF to HF (Spectral Ratio) of the amplitude and heart rate;

As indicated above, in the preferred embodiment described below, the sensor is a PAT sensor for application to a digit of the subject, and all the features determined by the analyzing operation are utilized to determine whether the epoch detected is a light-sleep epoch or a deep-sleep epoch.

The method and apparatus of the present invention, particularly when used with the method and apparatus described in the above-cited patent application Ser. No. 10/195,464, can be utilized for detecting all the sleep stages without the need of special sensors (e.g., EEG sensors) or other special equipment normally available in a sleep laboratory, and therefore can be used for unattended ambulatory sleep monitoring. This capability of the present invention has been favorably tested by a study comparing the results produced by the method and apparatus of the present invention with the results produced in a conventional sleep laboratory, as will be described more particularly below.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiment described is for purposes of example only, and that the invention is capable of being embodied in other forms and applications than described herein.

DESCRIPTION OF A PREFERRED
EMBODIMENT OF THE INVENTION

Figure 1:
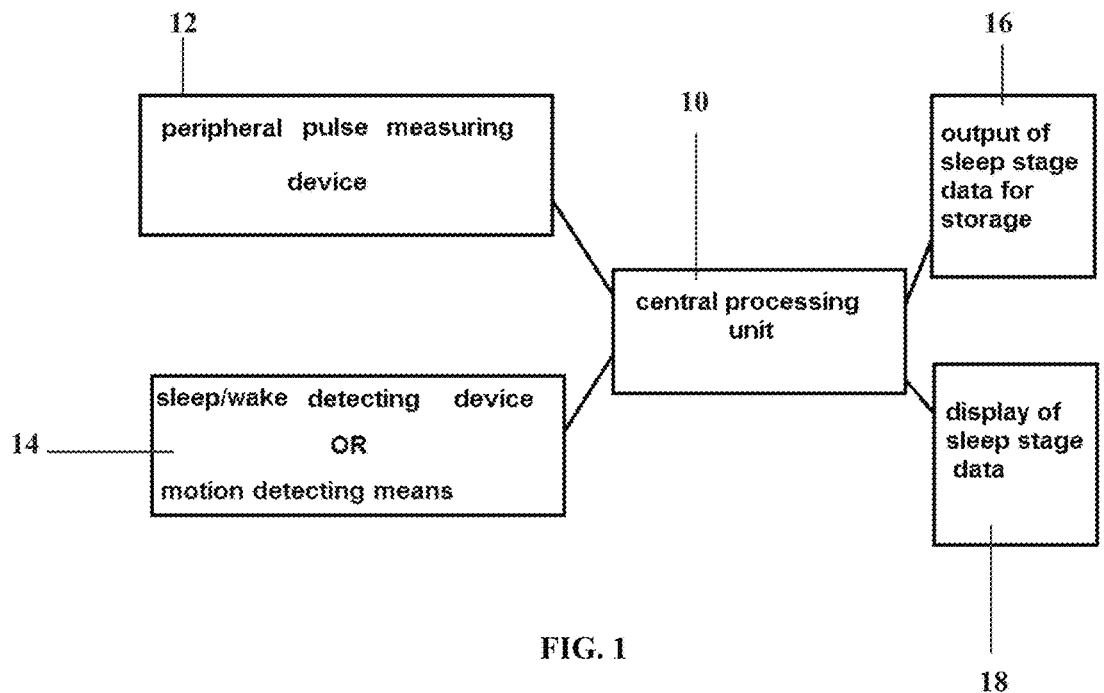
FIG. 1 is a block diagram illustrating the main components of one form of apparatus constructed in accordance with the present invention.
Figure 2:
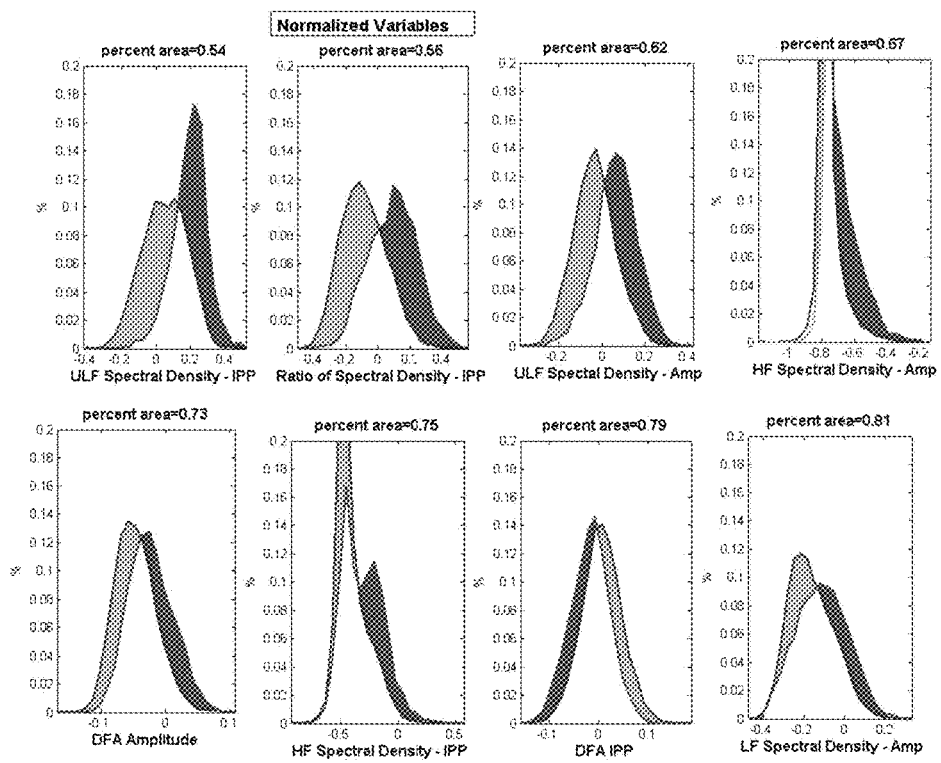
FIG. 2 is a flowchart showing the manner in which data is processed to determine sleep stages according to the preferred embodiment of the invention described herein.

FIG. 1 is a block diagram illustrating the main components of one form of apparatus constructed in accordance with the present invention; and FIG. 2 is a flowchart showing the manner in which data is obtained and processed to determine sleep stages according to the described embodiment of the invention.

Thus, as shown in FIG. 1, the apparatus includes a central processing unit, generally designated 10, having one input from a peripheral pulse measurement device 12 and another input from a sleep/wake detecting device or motion detecting devices 14. This information is processed by the central processing unit 10 to produce a data output 16 representing the sleep stage data for storage, and a display output 18 for displaying the sleep stage data.

Input device 12 is a sensor for sensing a peripheral pulse signal from the subject related to the systemic circulation of the subject. The peripheral pulse measuring device 12 may be any known device for detecting such signals, but preferably is a PAT probe applied to a digit (finger or toe) of the subject for measuring the peripheral arterial tone and the pulse rate of the subject. Many such PAT sensors are known in the art, for example as described in the above-cited U.S. patent application Ser. Nos. 10/195,464, 10/471,580, and 10/520,273, incorporated herein by reference and assigned to the same assignee as the present application.

The sleep/wake detecting device 14 may be a conventional Actigraph probe applied to the wrist, or to any other part of the patient's body surface if some adaptation to the initial algorithm is made and if the same sensitivity to movement is kept. Alternatively, it may be a motion detecting device, such as an accelerometer-type sensor, applied to the subject for detecting body movements.

The central processing unit 10 processes the data inputted by input units 12 and 14 according to the algorithm described below, particularly with respect to the flowchart of FIG. 3, to produce a data output 16 of the sleep stage data for storage or other processing control, and also a display output 18 of the sleep stage data.

Figure 3:
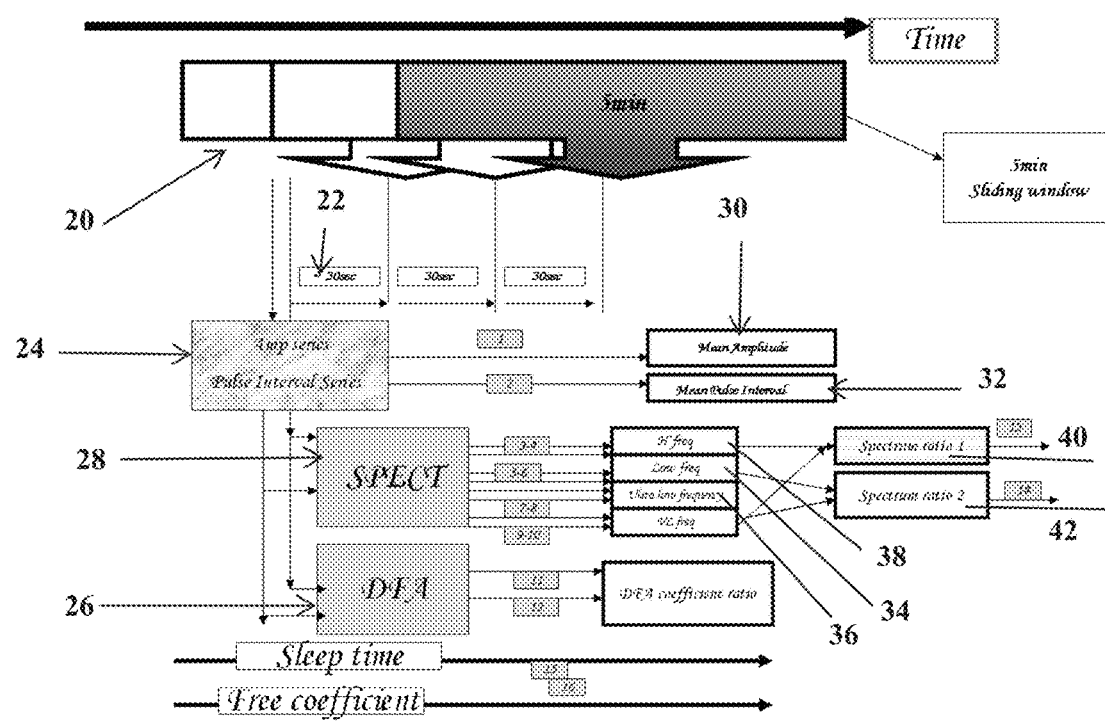
FIG. 3 illustrates histograms of separations for the variables that demonstrate the best separation (after NF)

The flowchart illustrated in FIG. 3, describing the algorithm of the central processing unit 10, receives the peripheral pulse signal sensed from the subject related to the system circulation of the subject, analyzes the peripheral pulse signal sensed for determining therefrom a number of features as described below and as illustrated in FIG. 3, and utilizes the results of the analysis to determine the probability that a specific sleep epoch is a deep-sleep or a light-sleep epoch. All the variables and their conditional probabilities are computed within a five-minute sliding window, as shown at 20, advanced by 30 second epochs, as shown at 22.

As further shown in FIG. 3, a set of 14 normalized variables in both the frequency and time domains (7 in each domain) are derived from features of the PAT signal amplitude (AMP) time series and the heart-rate, i.e. inter-pulse (IPP), time series as indicated by block 24. All the variables are scaled to their mean value so that they could be interpreted as a conditional probability. From each of the time series, a set of seven similar types of variables are derived, making it total of 14 variables, as indicated by blocks 1-16 in FIG. 3. Each such set of seven variables includes: (1) scaling coefficients of detrended fluctuation analysis (DFA) as indicated by block 26; (2) the mean value (AMP in block 30)(heart rate in block 32); (3) the peak of the low frequency spectral density (LF) (block 34); (4) the peak of the very low frequency spectral density (VLF); (5) the peak of the ultra-low frequency spectral density (ULF) (block 36); (6) the peak of the high frequency spectral density (HF) (block 38); and (7) the ratio of LF to HF (Spec Ratio) (blocks 28, 40, 42).

The central processing unit 10 further utilizes the results of the foregoing analyses to determine whether each 30-second epoch within the 5-minute slotting window is probably a light-sleep epoch or a deep-sleep epoch.

As said before, each such type of variable is derived from each of the two time series. The frequency ranges, corresponding to the respiratory, baro-receptor, thermoregulation and hormonal ranges, are 0.4-0.15 Hz (HF), 0.15-0.04 Hz (LF), 0.04-0.015 Hz (VLF) and 0.015-0.005 Hz (ULF) (Burgess et al 2004).

To combine and weigh each of the features we performed a 2 step algorithm. The first step was to filter each of the features by defining a ±5 minutes window around each epoch, allowing for smoothing around the epoch under consideration. This filter is defined as a Neighboring Filter (NF). The second step was done by choosing weightings that minimize the differences between the PSG staging and the PAT derived staging. Each feature was examined for the degree to which it differentiates between light and deep sleep, prior and after the filtering.

The total probability equation can be written as follows:

$$Y_{est}(n) = \sum_{j=1}^{14} \sum_{k=-10}^{10} W_{jk} * X_j(n+k) \quad \text{Eq. (1)}$$

Where:

$Y_{est}(n)$ is the Probability of an epoch n to be a deep sleep epoch;

$Xj(n)$ is the value of each one of the 14 variables at epoch n;

and $W_{jk}$ is the 21 filter coefficients of each epoch k within the sliding window centered around epoch n.

The weights are computed analytically to minimize the error in the identification process. The minimization criteria and weights computation method can be express by the following equation:

$$W_{jk} = \text{Min}\left(\sum_{n=1}^{N} Y_{est\_n} - Y_{actual\_n}\right)^2 \quad \text{Eq. (2)}$$

Where terms also occurring in equation 1 have the same definitions, and $Y_{actual}$ is "1" if the n epoch is deep, and "0" otherwise.

The least squares error between the stage estimates $Y_{est}$ and the PSG stages) $Y_{actual}$ (a vector of length N corresponding to the PSG sleep stage of each epoch), Optimization was performed on a training set of 49 sleep studies. Rather than optimizing each estimator ($W_{jk}$) separately, the algorithm uses a single level of optimization wherein a linear classifier acts on an enlarged variable set composed of 20 epochs for every variable.

Testing the Described Embodiment

Subjects

For purposes of testing the described embodiment, a study was conducted in which the study group consisted of two separate sets: A training set, used to develop the algorithm, and a separate validation set, used to validate the algorithms. The raining set consisted of 49 adult patients (27 males) referred to the Technion Sleep Disorders Center for evaluation of presumed obstructive sleep apnea syndrome (OSAS), and an additional 6 young healthy volunteers (3 males) without any complaints of sleep disruption, daytime sleepiness, or snoring, recruited via advertisements in the Faculty of Medicine of the Technion, Haifa. The healthy volunteers were free of any disease and were on no medications. The exclusion criteria for the suspected OSAS patients were: permanent pacemaker, non-sinus cardiac arrhythmias, peripheral vasculopathy or neuropathy, severe lung disease, S/P Bilateral cervical or thoracic sympathectomy, finger deformity that precluded adequate sensor application, use of alpha-adrenergic receptor blockers (24 hours washout period required), alcohol or drug abuse during the last 3 years.

The validation set consisted of 44 adult OSAS patients (30 males), and 10 young healthy volunteers (8 males) recruited in the same manner as the training set and according to the same inclusion and exclusion criteria. The study was approved by the Rambam Medical Center committee for studies in human subjects, and patients signed an informed consent form prior to participation.

The training and validation groups did not differ statistically in RDI, age, BMI Desaturation index, mean SAO2 values, arousal index percent of Deep Sleep percent of REM sleep and total sleep time (see Table 1).

|  | Training Set (N = 49) | Validation Set (N = 44) | P Value |
| --- | --- | --- | --- |
| Mean RDI | 26.9 ± 19.09 | 34.0 ± 30.28 | NS |
| Mean Age | 44.7 ± 13.58 | 43.5 ± 14.67 | NS |
| Mean BMI | 27.4 ± 5.31 | 28.7 ± 6.23 | NS |
| Mean arousal index | 33. ± 22 | 26.6 ± 14. | NS |
| Mean deep % | 21 ± 9 | 20.9 ± 10 | NS |
| Mean REM % | 21 ± 7 | 19.4 ± 6 | NS |
| Total Sleep time [min.] | 351 ± 49 | 357 ± 61 | NS |
| mean SaO2 | 86 ± 19 | 84 ± 21 | NS |
| De-saturation index | 22 ± 23 | 21 ± 23 | NS |
| Sleep efficiency | 0.83 ± 11 | 0.84 ± 15 | NS |

Protocol

All participants underwent a whole night polysomnography (PSG, Embla system, Flaga HF, Iceland) with simultaneous recordings of the Watch-PAT (WP) device (Itamar-Medical LTD, Caesarea, Israel). The PSG and the WP were synchronized using a continuous synchronization bi-level signal generated by the WP and recorded on both devices. The 2 sets of signals (the one from the PSG and the one from the WP) were then synchronized to compensate differences in internal clock of the 2 systems. The final error in synchronization time does not exceed 20 sec. By the end of the recording, the two data files (in PSG and in Watch-PAT) included the same synchronization signal and could thus be aligned exactly off line for head to head comparisons.

Prior to the study, patients completed a sleep questionnaire including physical data (e.g. weight and height), general health condition and medical history, medication usage, and sleep habits. Lights off were no later than midnight, and lights on at 06:00 AM. The mean start time of the test was 11 PM±30 min and the end of the test was 6:00±45 min and the mean duration was 7.99±42 min The WP was attached to the forearm of the dominant hand of the patient. The PAT probe was mounted on the index finger and the oximetry probe on the adjacent finger. Recording started with lights off and continued in a synchronized mode till lights on. The data quality of both the WP and the PSG were quite good and the signals recorded were valid for about 90% of the study.

The PSG files were scored for Apnea-Hypopnea index using Chicago criteria. Data was blindly double scored for stages to assess inter-scorer variability. The kappa coefficient for the stages double scoring was 0.83—which is considered "Almost perfect agreement" according to Landis and Koch (1977).

In-Laboratory WP Recording

The WP device has been previously described, (Bar et al., 2003; Hedner et al., 2004; Margel et al., 2003; Penzel et al., 2004; Penzel et al., 2004; Pillar et al., 2003). Briefly, it consists of a battery-powered, wrist-mounted recording device and software for post-acquisition viewing and analysis of the recorded PAT data, which are derived from a specialized finger probe which records the arterial pulse. It records 4 signals: PAT signal (arterial pulse wave amplitude), pulse rate derived from the PAT signal, oxyhemoglobin saturation, and wrist activity (derived from an accelerometer). The WP device contains a rechargeable power supply, preliminary signal conditioning hardware, 100 Hz data acquisition, and data storage on a removable compact flash disk.

In-Laboratory Polysomnography

All subjects underwent a standard in-laboratory overnight PSG. Recorded signals included: EEG (C4-A1, C3-A2, O2-A1 and O1-A2), EOG, sub-mental and bilateral tibial EMG, ECG, airflow (nasal pressure and thermistor), chest and abdominal motion (piezo bands), oxyhemoglobin saturation, positive airway pressure, and body position. All physiological data were collected and stored on the digital polysomnography system (Embla, Flaga, Reykjavik, Iceland). PSG recordings were scored manually, with the scorer being blinded to the PAT signals. Sleep was blindly staged on the PSG according to standard R&K criteria and applying the updated AASM Visual Scoring Task Force criterion to combine the stages 3 and 4 into one deep sleep stage (Rechtschaffen and Kales, 1968; Silber et al., 2007).

PAT Algorithms Description

The WP system is already equipped with a set of algorithms, well described in the literature, detecting Sleep, Wake, and REM states using actigraphy and PAT signal, with an epoch by epoch high resolution performance (Hedner et al., 2004, Herscovici et all 2007). The newly developed algorithm described in the current study is intended to further separate the non-REM epochs, and classify them into deep or light-sleep epochs. The actigraph is used to differentiate between sleep and wake periods only and not used for differentiation within the sleep periods between REM, deep and light-sleep stages and neither is the oximeter.

A set of 14 normalized variables in both the frequency and time domains were derived from the PAT signal amplitude (AMP) time series and the Heart Rate, i.e. inter-pulse period (IPP) time series (seven from each time series), and utilized to determine whether a particular epoch detected was probably a light-sleep epoch or a deep-sleep epoch in the manner described above with respect to Equations (1) and (2). All the variables and their conditional probabilities were computed within a 5 minute sliding window advanced by 30 seconds epochs.

Analysis Method

The algorithm accuracy was assessed by applying the weighted coefficient computed from the training set to the validation set.

The PAT studies were analyzed using the Actigraph algorithm to separate the sleep and wake periods using previously described algorithms (Hedner et al, 2004). The REM periods were detected using the previously described REM algorithm (Herscovici et al., 2007). The Non-REM periods were then separated into deep and light-sleep periods using the newly developed algorithm. The oximetry measurement is not used to differentiate between deep and light neither the actigraph. The comparison was done based on a 30 sec epoch by epoch comparison. Comparisons of performance in different OSA severity groups were made to show that the algorithm is not impaired by OSA severity effects on the PAT signal. The Algorithm performance was evaluated for each RDI group stratified by mild (0-20), moderate (20-40), and severe (more than 40).

The total sensitivity specificity and agreement were measured using the whole 27,597 (20,555 Light-sleep and 7,042 Deep sleep) from the PSG epochs for training and 24,383 (18,320 Light-sleep and 6063 Deep Sleep) epochs for validation. Mean values of sensitivity specificity and agreement based on per subject value were also computed as well as Kappa Cohen agreement Results Training Data Set FIG. 2 shows the normalized histogram of the 8 major contributive variables with the relative separation of each.

In FIG. 2, the histograms of separations for the variables demonstrate the best separations (after NF). The best separation is given in the upper left panel and decreases clockwise. The dark shaded region represents complete separation of deep sleep. The lighter shaded region represents complete separation of light-sleep and the un-shaded area in between represents un-separation (overlap of the two). The value on top of the graph represents the un-separated area relative to deep sleep complete separation area (a lower ratio means better separation).

TABLE 2 sensitivity specificity and agreement mean values by subject for the three groups

|  | Group 1<br>RDI < 20 | Group 2<br>20 < RDI < 40 | Group 3<br>RDI > 40 |
|---|---|---|---|
| Sensitivity[%] | 61 ± 26 | 55 ± 23 | 72 ± 32 |
| Specificity[%] | 89 ± 10 | 87 ± 13 | 87 ± 6 |
| Agreement[%] | 82 ± 7 | 78 ± 13 | 85 ± 6 |

Figure 4:
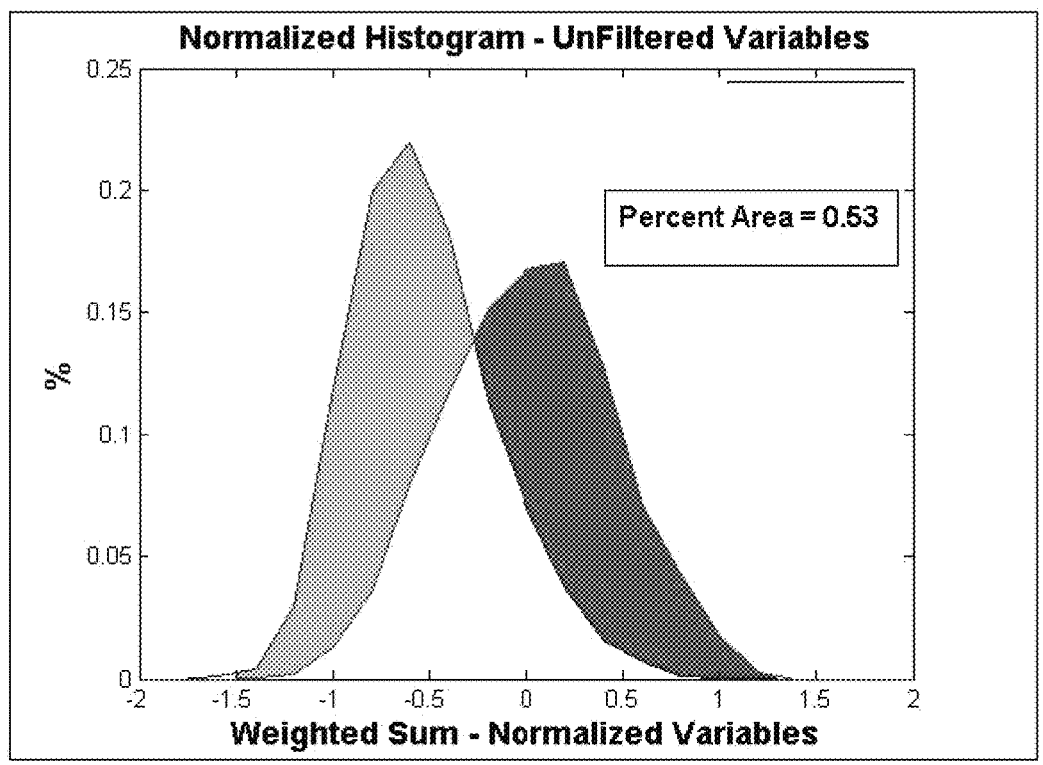
FIG. 4 is a diagram illustrating the weighted sum distribution without NF.
Figure 5:
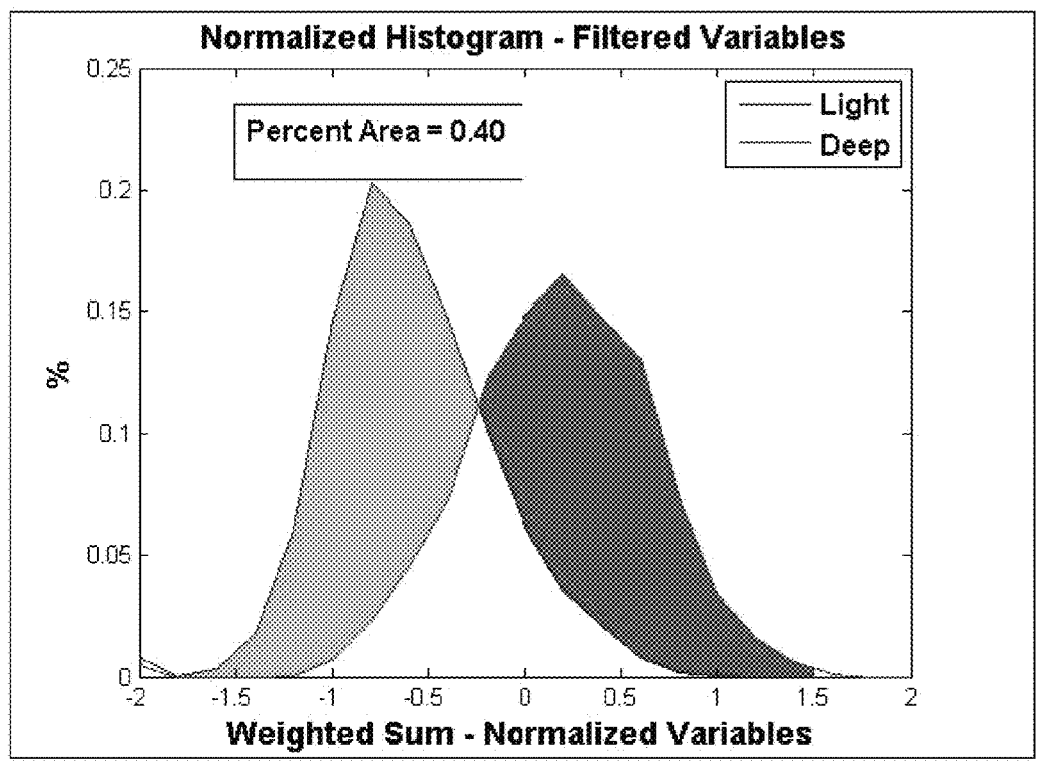
FIG. 5 is a diagram illustrating the weighted sum distribution with NF.

FIG. 4 shows the combined histogram of all the variables (14 variables) for the combined data of all the patients for deep and light-sleep, and illustrates the separation without filtration, and FIG. 5 shows the separation including the NF. The filtered data improves the separation between stages by 2% in sensitivity and 8% in specificity. Without filters the sensitivity/specificity is 72% and 77% respectively (threshold −0.325). By adding the filter, the sensitivity and specificity increase to 74% and 85% when choosing the threshold at the intersection point (threshold −0.2).

The last step is to choose a threshold for the clinical application. The threshold was chosen in order to bring up the total specificity on an ROC curve to approximately 90%. (Threshold 0.1) The one chosen yields in the training set sensitivity, specificity and agreement values of 66%, 89% and 82% respectively for the whole training set. The per subject mean values of the sensitivity specificity and agreement were (63%±89%±0.83±) respectively for the whole training set the Kappa Cohen coefficient was 0.52 (moderate agreement). mean value of Kappa averaging patients in each group is (0.52±0.17, 0.56±0.20 and 0.55±0.28) for light, moderate and severe RDI groups respectively.

Figure 6:
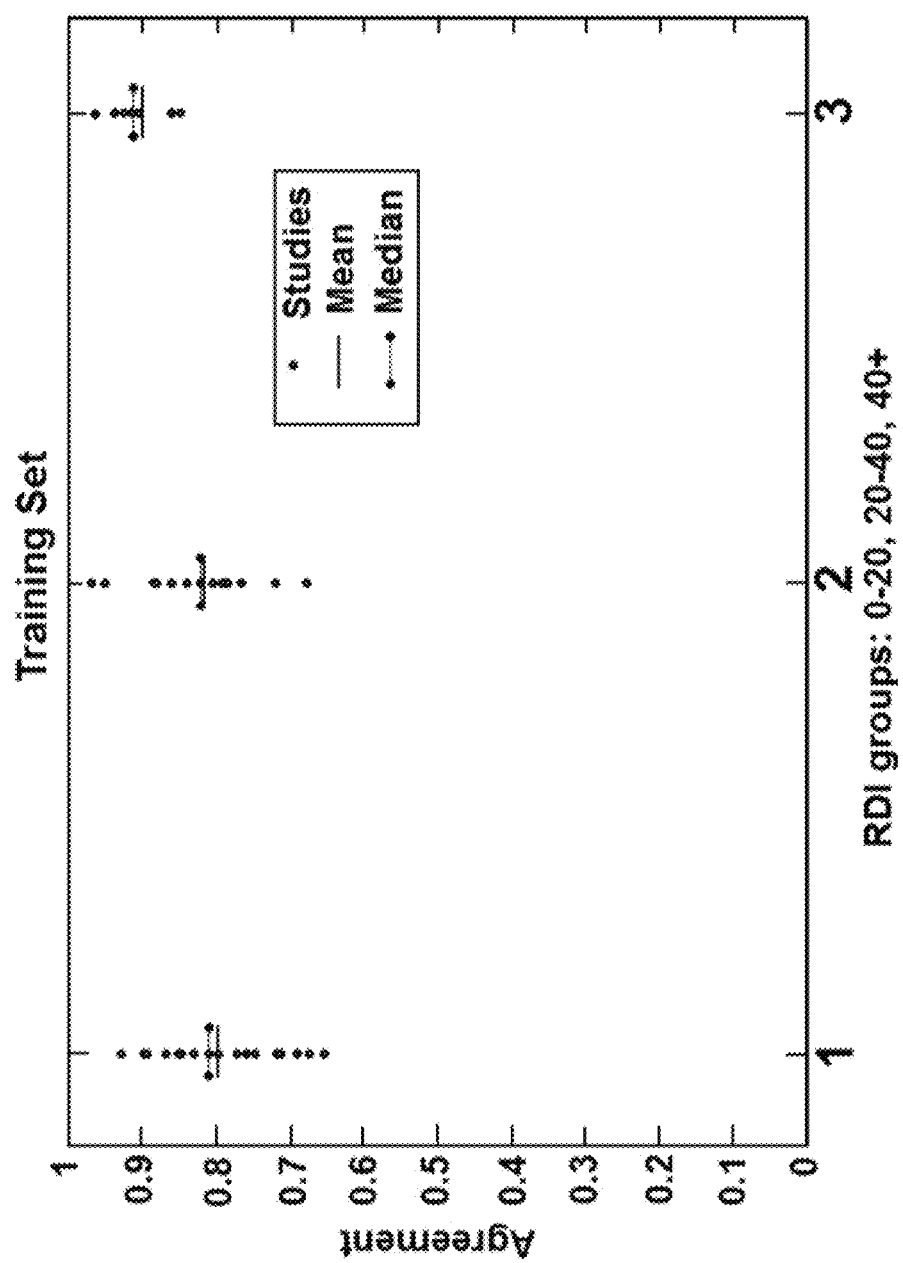
FIG. 6 is a diagram illustrating agreement for mild (1), moderate (2), and severe (3) OSA training set.
Figure 7:
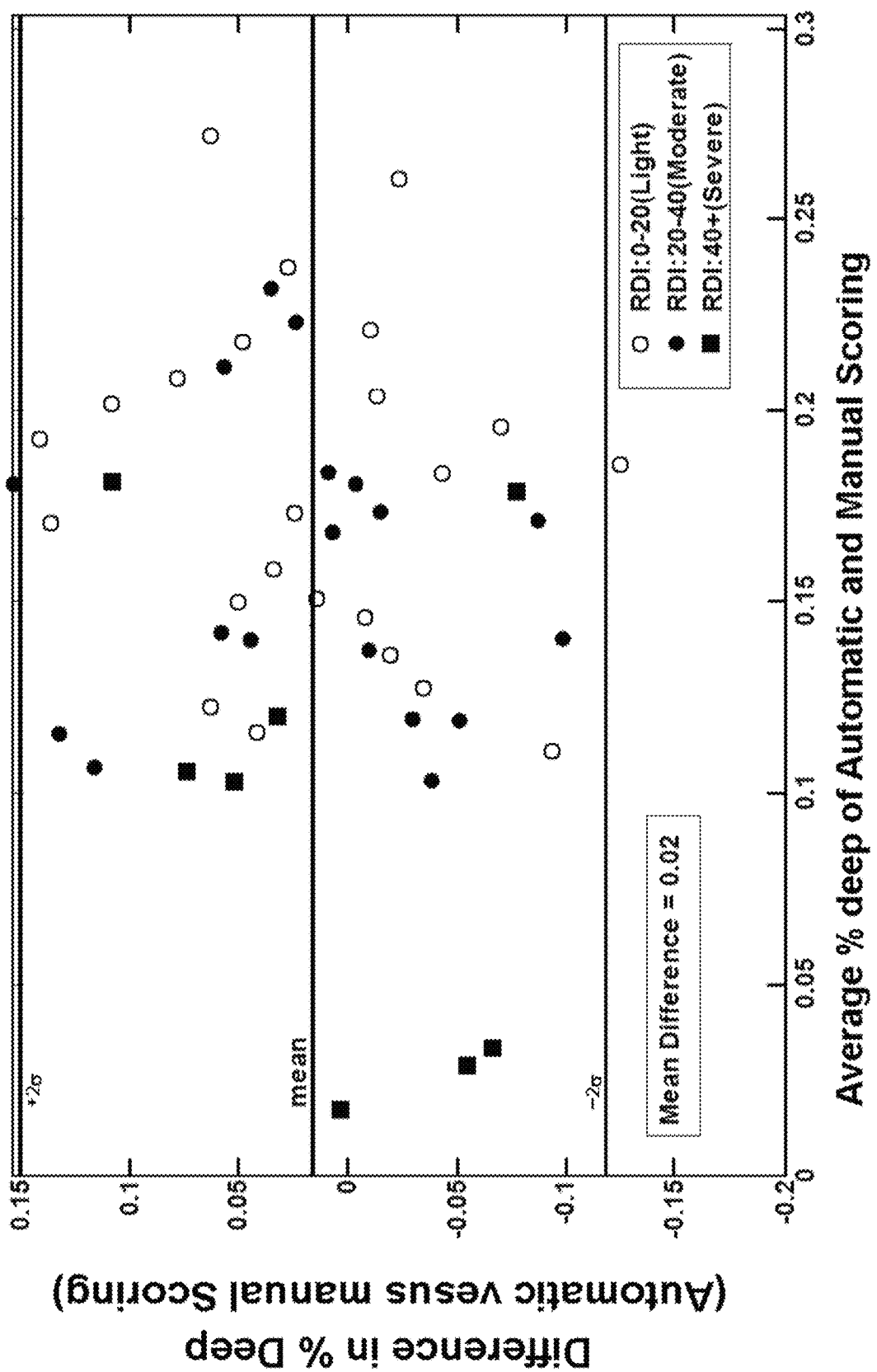
FIG. 7 is a diagram illustrating the Bland Altman plot, of the percent deep sleep stage detection (PSG first algorithm) for the training set.

FIG. 6 shows the total agreement of all the training set stratified to RDI categories. It can be seen that there is no substantial difference between the severe, mild and moderate OSA patient groups. The Bland Altman plot shown in FIG. 7 shows no offset and no systemic error in the results.

Validation Data Set

In order to assess the accuracy of the algorithm it was tested on a separate validation set of 44 studies, reflecting a broad range of sleep apnea severity. The whole validation set shows 65%, 87% and 80% sensitivity specificity and agreement values respectively. The mean value of sensitivity specificity and agreement of all the patients is 56% 87% and 81 respectively. The total sensitivity, specificity, and agreement values for the training set were very similar at 66%, 89% and 82% respectively. The correlation of percent of deep sleep over the night with the PSG was R=0.51 (P<0.05) for the whole validation set. The per subject mean values of the sensitivity specificity and agreement were (56%±87%±0.81±) respectively for the whole validation set the Kappa Cohen coefficient was 0.57 (moderate agreement). Mean value of Kappa averaging patients in each group is (0.46±0.19, 0.42±0.1 and 0.54±0.3) for light, moderate and severe RDI groups respectively.

Figure 8:
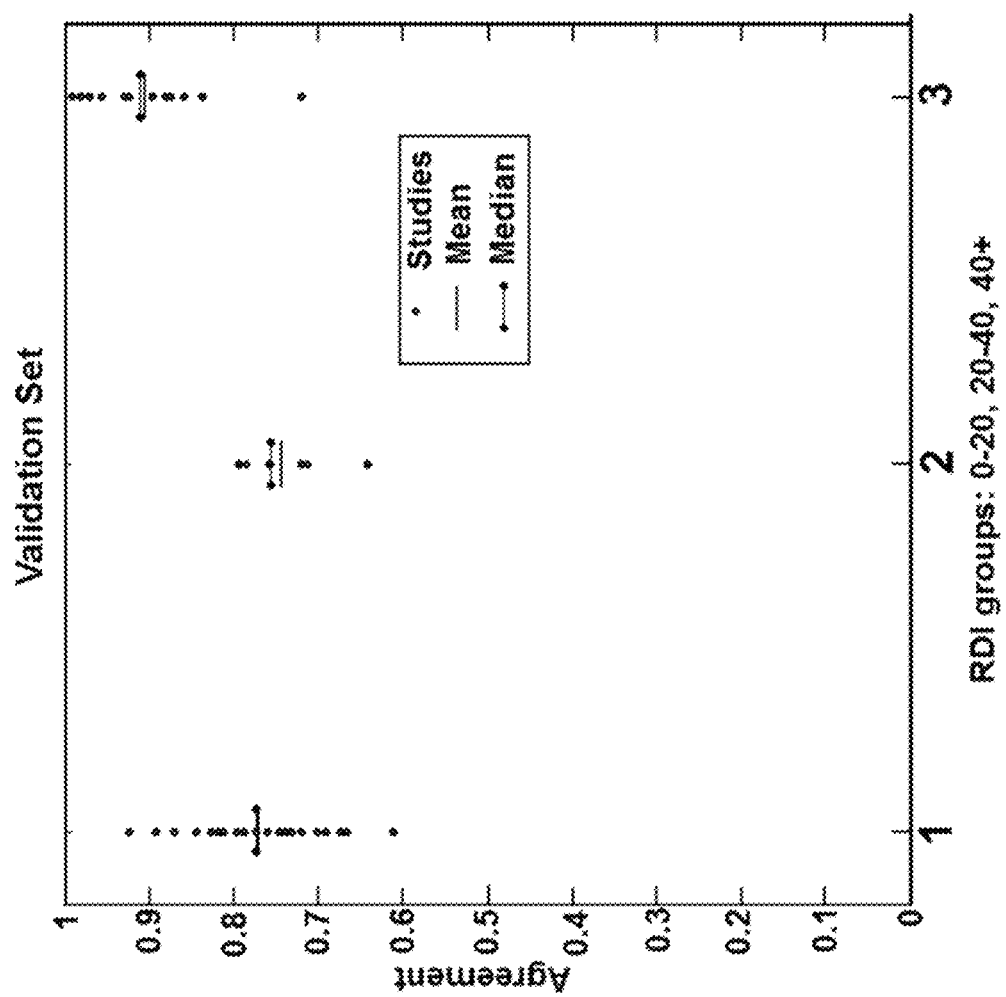
FIG. 8 is a diagram illustrating the agreement for mild (1), moderate (2), and severe (3) OSA validation sets.
Figure 9:
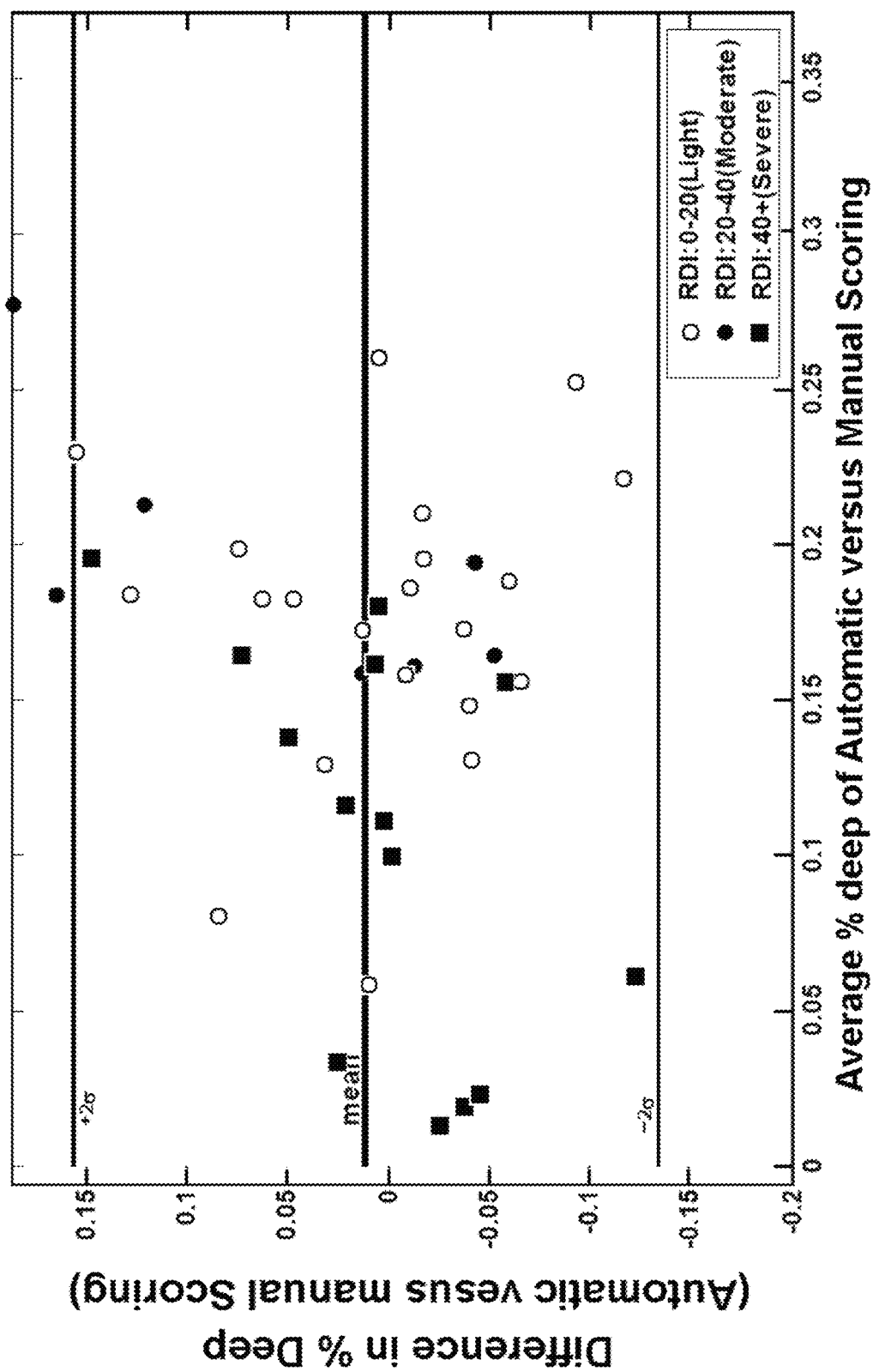
FIG. 9 is a Bland Altman plot of error in percent deep sleep stage detection (PSG versus algorithm developed herein) for the validation set.

FIG. 8 shows the total agreement of all the training set stratified to RDI categories. It can be seen that there is no substantial difference between the severe, mild and moderate OSA patient groups FIG. 9 shows the Bland Altman plot of the percent deep sleep for the validation set. There is no systemic error in percent deep sleep.

The above evaluations show that the described algorithm which is based on the PAT signal, or other known peripheral pulse signal, is capable of detecting light and deep sleep stages. Used together with previously known algorithms to detect sleep/wake, non-REM and REM sleep, e.g., as described in their prior patents cited above, it is believed that the present inventive method and apparatus, enable a comprehensive sleep stage assessment to be provided without the special equipment, such as EEG sensors, normally available only in sleep laboratories.

While the invention has been described with respect to one preferred embodiment, it will be appreciated that this is set forth merely for purposes of example, and that many variations, modifications and other applications of the invention may be made.

REFERENCES

Aydin, M., Altin, R., Ozeren, A., Kart, L., Bilge, M., and Unalacak, M. (2004). Cardiac autonomic activity in obstructive sleep apnea: time-dependent and spectral analysis of heart rate variability using 24-hour Holter electrocardiograms. *Tex Heart Inst J* 31, 132-6.

Bar, A., Pillar, G., Dvir, I., Sheffy, J., Schnall, R. P., and Lavie, P. (2003). Evaluation of a portable device based on peripheral arterial tone for unattended home sleep studies. *Chest* 123, 695-703.

Berlad, I. I., Shlitner, A., Ben-Haim, S., and Lavie, P. (1993). Power spectrum analysis and heart rate variability in Stage 4 and REM sleep: evidence for state-specific changes in autonomic dominance. *J Sleep Res* 2, 88-90.

Bonnet, M. H., and Arand, D. L. (1997). Heart rate variability: sleep stage, time of night, and arousal influences. *Electroencephalogr Clin Neurophysiol* 102, 390-6.

Brandenberger, G., Ehrhart, J., and Buchheit, M. (2005). Sleep stage 2: an electroencephalographic, autonomic, and hormonal duality. *Sleep* 28, 1535-40.

Brooks, D., Horner, R. L., Floras, J. S., Kozar, L. F., Render-Teixeira, C. L., and Phillipson, E. A. (1999). Baroreflex control of heart rate in a canine model of obstructive sleep apnea. *Am J Respir Crit Care Med* 159, 1293-7.

Burgess, H. J., Trinder, J., and Kim, Y. (1999). Cardiac autonomic nervous system activity during presleep wakefulness and stage 2 NREM sleep. *J Sleep Res* 8, 113-22.

Burgess H J, Penev P D, Schneider R, Van Cauter E. Estimating cardiac autonomic activity during sleep: impedance cardiography, spectral analysis, and Poincare plots. *Clin Neurophysiol* 2004; 115:19-28.

Busek, P., Vankova, J., Opavsky, J., Salinger, J., and Nevsimalova, S. (2005). Spectral analysis of the heart rate variability in sleep. *Physiol Res* 54, 369-76.

Chesson, A. L. J., Berry, R. B., and Pack, A. (2003). American Academy of Sleep Medicine; American Thoracic Society; American College of Chest Physicians. Practice parameters for the use of portable monitoring devices in the investigation of suspected obstructive sleep apnea in adults. *Sleep* 23, 907-13.

Collop, N. A. (2002). Scoring variability between polysomnography technologists in different sleep laboratories. *Sleep Med* 3, 43-7.

Dvir, I., Adler, Y., Freimark, D., and Lavie, P. (2002). Evidence for fractal correlation properties in variations of peripheral arterial tone during REM sleep. *Am J Physiol Heart Circ Physiol* 283, H434-9.

Elsenbruch, S., Hamish, M. J., and Orr, W. C. (1999). Heart rate variability during waking and sleep in healthy males and females. *Sleep* 22, 1067-71.

Ferri, R., Parrino, L., Smerieri, A., Terzano, M. G., Elia, M., Musumeci, S. A., and Pettinato, S. (2000). Cyclic alternating pattern and spectral analysis of heart rate variability during normal sleep. *J Sleep Res* 9, 13-8.

Flemons, W. W., Littner, M. R., Rowley, J. A., Gay, P., Anderson, W. M., Hudgel, D. W., McEvoy, R. D., and Loube, D. I. (2003). Home diagnosis of sleep apnea: a systematic review of the literature. An evidence review cosponsored by the American Academy of Sleep Medicine, the American College of Chest Physicians, and the American Thoracic Society. *Chest* 124, 1543-79.

Futuro-Neto, H. A., and Coote, J. H. (1982). Changes in sympathetic activity to heart and blood vessels during desynchronized sleep. *Brain Res* 252, 259-68.

Hedner, J., Pillar, G., Pittman, S. D., Zou, D., Grote, L., and White, D. P. (2004). A novel adaptive wrist actigraphy algorithm for sleep-wake assessment in sleep apnea patients. *Sleep* 27, 1560-6.

Herscovici, S., Pe'er, A., Papyan, S., and Lavie, P. (2007). Detecting REM sleep from the finger: an automatic REM sleep algorithm based on peripheral arterial tone (PAT) and actigraphy. *Physiol Meas* 28, 129-40.

Hornyak, M., Cejnar, M., Elam, M., Matousek, M., and Wallin, B. G. (1991). Sympathetic muscle nerve activity during sleep in man. *Brain* 114 (Pt 3), 1281-95.

Jo, J. A., Blasi, A., Valladares, E., Juarez, R., Baydur, A., and Khoo, M. C. (2005). Determinants of heart rate variability in obstructive sleep apnea syndrome during wakefulness and sleep. *Am J Physiol Heart Circ Physiol* 288, H1103-12.

Kirby, D. A., and Verrier, R. L. (1989). Differential effects of sleep stage on coronary hemodynamic function. *Am J Physiol* 256, H1378-83.

Kodama, Y., Iwase, S., Mano, T., Cui, J., Kitazawa, H., Okada, H., Takeuchi, S., and Sobue, G. (1998). Attenuation of regional differentiation of sympathetic nerve activity during sleep in humans. *J Auton Nerv Syst* 74, 126-33.

Lavie, P., Pillar, G., and Malhotra, A. (2002). Sleep Disorders: Diagnosis and Treatment. *A handbook for the clinician* Martin Dunitz L.T.D., London.

Lavie, P., Schnall, R. P., Sheffy, J., and Shlitner, A. (2000). Peripheral vasoconstriction during REM sleep detected by a new plethysmographic method. *Nat Med* 6, 606.

Levy, P., and Pepin, J. L. (2003). Sleep fragmentation: clinical usefulness of autonomic markers. *Sleep Med* 4, 489-91.

Liguori, R., Donadio, V., Foschini, E., Di Stasi, V., Plazzi, G., Lugaresi, E., and Montagna, P. (2000). Sleep stage-related changes in sympathetic sudomotor and vasomotor skin responses in man. *Clin Neurophysiol* 111, 434-9.

Malhotra, A., and White, D. P. (2002). Obstructive sleep apnoea. *Lancet* 360, 237-45.

Margel, D., White, D. P., and Pillar, G. (2003). Long-term intermittent exposure to high ambient CO2 causes respiratory disturbances during sleep in submariners. *Chest* 124, 1716-23.

Monti, A., Medigue, C., Nedelcoux, H., and Escourrou, P. (2002). Autonomic control of the cardiovascular system during sleep in normal subjects. *Eur J Appl Physiol* 87, 174-81.

Narkiewicz, K., Montano, N., Cogliati, C., van de Borne, P. J., Dyken, M. E., and Somers, V. K. (1998). Altered cardiovascular variability in obstructive sleep apnea. *Circulation* 98, 1071-7.

Narkiewicz, K., and Somers, V. K. (1997). The sympathetic nervous system and obstructive sleep apnea: implications for hypertension. *J Hypertens* 15, 1613-9.

Narkiewicz, K., van de Borne, P. J., Cooley, R. L., Dyken, M. E., and Somers, V. K. (1998). Sympathetic activity in obese subjects with and without obstructive sleep apnea. *Circulation* 98, 772-6.

Negoescu, R. M., and Csiki, I. E. (1989). Autonomic control of the heart in some vagal maneuvers and normal sleep. *Physiologie* 26, 39-49.

Noll, G., Elam, M., Kunimoto, M., Karlsson, T., and Wallin, B. G. (1994). Skin sympathetic nerve activity and effector function during sleep in humans. *Acta Physiol Scand* 151, 319-29.

Norman, R. G., Pal, I., Stewart, C., Walsleben, J. A., and Rapoport, D. M. (2000). Interobserver agreement among sleep scorers from different centers in a large dataset. *Sleep* 23, 901-8.

Okada, H., Iwase, S., Mano, T., Sugiyama, Y., and Watanabe, T. (1991). Changes in muscle sympathetic nerve activity during sleep in humans. *Neurology* 41, 1961-6.

Penzel, T., Bunde, A., Grote, L., Kantelhardt, J. W., Peter, J. H., and Voigt, K. (2000). Heart rate variability during sleep stages in normals and in patients with sleep apnea. *Stud Health Technol Inform* 77, 1256-60.

Penzel, T., Kantelhardt, J. W., Grote, L., Peter, J. H., and Bunde, A. (2003). Comparison of detrended fluctuation analysis and spectral analysis for heart rate variability in sleep and sleep apnea. *IEEE Trans Biomed Eng* 50, 1143-51.

Penzel, T., Kesper, K., Pinnow, I., Becker, H. F., and Vogelmeier, C. (2004). Peripheral arterial tonometry, oximetry and actigraphy for ambulatory recording of sleep apnea. *Physiol Meas* 25, 1025-36.

Penzel, T., Kesper, K., Ploch, T., Becker, H. F., and Vogelmeier, C. (2004). Ambulatory recording of sleep apnea using peripheral arterial tonometry. *Conf Proc IEEE Eng Med Biol Soc* 5, 3856-9.

Pepin, J. L., Veale, D., and Levy, P. A. (1994). Heart rate variability during sleep in snorers with and without obstructive sleep apnea. *Chest* 105, 1300-1.

Pillar, G., Bar, A., Betito, M., Schnall, R. P., Dvir, I., Sheffy, J., and Lavie, P. (2003). An automatic ambulatory device for detection of AASM defined arousals from sleep: the WP100. *Sleep Med* 4, 207-12.

Pillar, G., Malhotra, A., Fogel, R. B., Beauregard, J., Slamowitz, D. I., Shea, S. A., and White, D. P. (2000). Upper airway muscle responsiveness to rising PCO(2) during NREM sleep. *J Appl Physiol* 89, 1275-82.

Pressman, M. R., and Fry, J. M. (1989). Relationship of autonomic nervous system activity to daytime sleepiness and prior sleep. *Sleep* 12, 239-45.

Rechtschaffen, A., and Kales, A. (1968). A manual of standardized terminology, techniques and scoring system for sleep stages of human subjects. *Los Angeles: Brain Information Service/Brain Research Institute*.

Silber, M. H., Ancoli-Israel, S., Bonnet, M. H., Chokroverty, S., Grigg-Damberger, M. M., Hirshkowitz, M., Kapen, S., Keenan, S. A., Kryger, M. H., Penzel, T., Pressman, M. R., and Iber, C. (2007). The visual scoring of sleep in adults. *J Clin Sleep Med* 3, 121-31.

Somers, V. K., Dyken, M. E., Mark, A. L., and Abboud, F. M. (1993). Sympathetic-nerve activity during sleep in normal subjects. *N Engl J Med* 328, 303-7.

Svetnik, V., Ma, J., Soper, K. A., Doran, S., Renger, J. J., Deacon, S., and Koblan, K. S. (2007). Evaluation of automated and semi-automated scoring of polysomnographic recordings from a clinical trial using zolpidem in the treatment of insomnia. *Sleep* 30, 1562-74.

Takeuchi, S., Iwase, S., Mano, T., Okada, H., Sugiyama, Y., and Watanabe, T. (1994). Sleep-related changes in human muscle and skin sympathetic nerve activities. *J Auton Nerv Syst* 47, 121-9.

Trinder, J., Kleiman, J., Carrington, M., Smith, S., Breen, S., Tan, N., and Kim, Y. (2001). Autonomic activity during human sleep as a function of time and sleep stage. *J Sleep Res* 10, 253-64.

Villa, M. P., Calcagnini, G., Pagani, J., Paggi, B., Massa, F., and Ronchetti, R. (2000). Effects of sleep stage and age on short-term heart rate variability during sleep in healthy infants and children. *Chest* 117, 460-6.

Virtanen, I., Ekholm, E., Polo-Kantola, P., and Huikuri, H. (2007). Sleep stage dependent patterns of nonlinear heart rate dynamics in postmenopausal women. *Auton Neurosci* 134, 74-80.

What is claimed is:

1. A computerized method for improving a capability of using a peripheral pulse measurement device, while not requiring sensors or other specialized instruments provided in a sleep laboratory, sensing a peripheral pulse signal at a body site of a subject, which is related to a systemic circulation of the subject, for detecting and distinguishing epochs of non-rapid eye movement (non-REM) deep-sleep from epochs of non-REM light-sleep of the subject, comprising:

using a hardware processor of a central processing unit for:

receiving from said peripheral pulse measurement device, which includes at least one sensor, the peripheral pulse signal sensed by the at least one sensor at the body site of the subject related to the systemic circulation of the subject for a period of a sleep epoch, said peripheral pulse signal is sensed during a time said subject is outside of a sleep laboratory;

analyzing the sensed peripheral pulse signal and detect when said sleep epoch is a non-REM sleep epoch;

using the sensed peripheral pulse signal to identify when said non-REM sleep epoch is a sleep stage of a non-REM light-sleep epoch and when the non-REM sleep epoch is a sleep stage of a non-REM deep-sleep epoch, by:

deriving, upon detection of said non-REM sleep epoch, from said sensed peripheral pulse signal, a plurality of variables, said plurality of variables including:

an at least first spectral density peak of a frequency range of an amplitude time series of said peripheral pulse signal, said at least first spectral density peak representing a vascular tone channel, and an at least second spectral density peak of a frequency range of a heart and/or pulse rate time series of said peripheral pulse signal;

applying a Neighboring Filter (NF) on the sensed peripheral pulse signal, said NF is defined on a time window spanning from a pre-defined time before said detected non-REM sleep epoch to a pre-defined time after said detected non-REM sleep epoch;

deriving from said filtered sensed peripheral pulse signal a plurality of filtered variables corresponding to each of said at least first spectral density peak of the frequency range of the amplitude time series and said at least second spectral density peak of the frequency range of the heart and/or pulse rate time series;

determining when the detected non-REM sleep epoch is the sleep stage of the non-REM light-sleep epoch and when the detected non-REM sleep epoch is the sleep stage of the non-REM deep-sleep epoch, by comparing a weighted combination of said plurality of filtered variables to a pre-defined threshold;

outputting a sleep stage data output of said sleep stage, for storage or other processing control; and displaying the sleep stage data output.

2. The computerized method according to claim 1 further includes using said hardware processor for receiving from a sleep/wake detecting device including at least another sensor for sensing an indication of whether the subject is asleep based on measurements by said another sensor applied to the subject.

3. The computerized method according to claim 1, wherein said period of sleep epoch is a plurality of epochs each of a period of seconds within a sliding window of minutes.

4. The computerized method according to claim 1, wherein said period of sleep epoch is a plurality of epochs each of a period of about 30 seconds within a sliding window of about five minutes.

5. The computerized method according to claim 1, wherein at least one of said at least first spectral density peak and said at least second spectral density peak is determined for each of a low (LF), very-low (VLF), ultra-low (ULF), and high (HF) frequency ranges.

6. The computerized method according to claim 1, wherein each of said at least first spectral density peak and said at least second spectral density peak is determined for each of a low (LF), very-low (VLF), ultra-low (ULF), and high (HF) frequency ranges.

7. The computerized method according to claim 6, wherein said plurality of variables further includes a spectral density peak ratio of LF to HF for at least one of the amplitude and said heart and/or pulse rate time series of the sensed peripheral pulse signal.

8. The computerized method according to claim 6, wherein said plurality of variables further includes a spectral density peak ratio of LF to HF for each of the amplitude and said heart and/or pulse rate time series of the sensed peripheral pulse signal.

9. The computerized method according to claim 8, wherein said plurality of variables further includes a mean of at least one of the amplitude and said heart and/or pulse rate time series of the sensed peripheral pulse signal.

10. The computerized method according to claim 8, wherein said plurality of variables further includes a mean amplitude and mean heart and/or pulse rate time series of the sensed peripheral pulse signal.

11. The computerized method according to claim 10, wherein said plurality of variables further includes a scaling coefficient of a detrended fluctuation analysis (DFA) of at least one of the amplitude and said heart-rate time series of the sensed peripheral pulse signal.

12. The computerized method according to claim 10, wherein said plurality of variables further includes scaling coefficients of a detrended fluctuation analysis (DFA) of each of the amplitude and said heart-rate time series of the sensed peripheral pulse signal.

13. The computerized method according to claim 12, wherein said sensed peripheral pulse signal is sensed by a peripheral arterial tone (PAT) sensor applied to a digit of the subject.

14. The computerized method according to claim 12, wherein said peripheral pulse signal is sensed from the subject during each of two time periods; and wherein each peripheral pulse signal is analyzed for each time period, and results of such analyses are utilized to determine when said detected non-REM sleep epoch during each of said two time periods is a non-REM light-sleep epoch or a non-REM deep-sleep epoch.

15. The computerized method according to claim 14, wherein said weighted combination represents a probability of a non-REM sleep epoch to be a non-REM deep sleep epoch, and is calculated according to the following equation:

$$Y_{est}(n) = \sum_{j=1}^{14} \sum_{k=-10}^{10} W_{jk} * X_j(n+k)$$

where:

Y(n) is a probability of an epoch n to be a non-REM deep sleep epoch;

$X_j(n)$ is a value of each one of the plurality of filtered variables, said plurality of filtered variables includes 14 variables at epoch n; and $W_{jk}$ are 21 filter coefficients of each epoch k within a sliding window centered around epoch n, said filter coefficients are computed analytically to minimize an error in said determination.

16. The computerized method of claim 1, wherein said plurality of variables further includes at least one of the group consisting of:

a spectral density peak ratio of LF to HF for at least one of the amplitude and heart and/or pulse rate time series of the sensed peripheral pulse signal, a mean amplitude or mean heart and/or pulse rate time series of the sensed peripheral pulse signal, and scaling coefficients of a detrended fluctuation analysis (DFA) of at least one of the amplitude and said heart and/or pulse rate time series of the sensed peripheral pulse signal.

17. A system for improving a capability of using a peripheral pulse measurement device, not requiring sensors or other specialized instruments provided in a sleep laboratory, sensing a peripheral pulse signal at a body site of a subject, which is related to a systemic circulation of the subject, for detecting and distinguishing non-rapid eye movement (non-REM) deep-sleep epochs from non-REM light-sleep epochs of the subject, comprising:
a central processing unit comprising a hardware processor adapted to:
analyze a peripheral pulse signal, sensed by a peripheral pulse measurement device which includes a sensor, said peripheral pulse signal is related to a systemic circulation of the subject, is sensed during a time said subject is outside of a sleep laboratory, and is received as an input from said peripheral pulse measurement device, to detect when a sleep epoch is a non-REM sleep epoch;
upon detection of said non-REM sleep epoch, derive from said sensed peripheral pulse signal, a plurality of variables,
apply a Neighboring Filter (NF) on said sensed peripheral pulse signal, said NF is defined on a time window spanning from a pre-defined time before said detected non-REM sleep epoch to a pre-defined time after said detected non-REM sleep epoch;
derive from said filtered sensed peripheral pulse signal a plurality of filtered variables;
determine when the detected non-REM sleep epoch is a sleep stage of a non-REM light-sleep epoch and when the detected non-REM sleep epoch is a sleep stage of a non-REM deep-sleep epoch by comparing a weighted combination of said plurality of filtered variables to a pre-defined threshold,
provide sleep stage data of said sleep stage as a data output by said central processing unit for representing said determined sleep stage of non-REM deep-sleep epoch or said determined sleep stage of non-REM light-sleep epoch to be used for storage or for other processing control, and
produce a display output for displaying said sleep stage data;
wherein, said plurality of variables includes:
an at least first spectral density peak of a frequency range of a time series of an amplitude of said peripheral pulse signal, said at least first determined spectral density peak representing a vascular tone channel, and
an at least second spectral density peak of a frequency range of a time series of a heart and/or pulse rate of said peripheral pulse signal; and
wherein said peripheral pulse signal is sensed by said peripheral pulse measurement device during a period of said sleep epoch of said subject.

18. The system according to claim 17, wherein said peripheral pulse signal is generated by a peripheral arterial tone (PAT) sensor included in said peripheral pulse measurement device, for application to a digit of the subject.

19. The system of claim 17, wherein said hardware processor is further adapted to receive a second input, from a sleep/wake detecting device, wherein the second input is an indication whether the subject is asleep.

20. The system according to claim 17, wherein said hardware processor is further adapted to conduct said analysis, said derivation of said plurality of variables, said application, said derivation of said plurality of filtered variables, said determination and said providing on each of a plurality of sleep epochs, each of said plurality of sleep epochs spans on a period of seconds, and wherein said plurality of sleep epochs occur within a sliding window of minutes.

21. The system according to claim 17, wherein said hardware processor is further adapted to conduct said analysis, said derivation of said plurality of variables, said application, said derivation of said plurality of filtered variables, said determination and said providing on each of a plurality of sleep epochs, each of said plurality of sleep epochs spans on a period of about 30 seconds, and wherein said plurality of sleep epochs occur within a sliding window of about five minutes.

22. The system according to claim 17, wherein said plurality of variables further includes spectral density peaks, determined for each of the low (LF), claim very-low (VLF), ultra-low (ULF), and high (HF) frequency ranges for at least one of the amplitude and heart and/or pulse rate time series of the sensed peripheral pulse signal.

23. The system according to claim 17, wherein said plurality of variables further includes spectral density peaks, determined for each of low (LF), very-low (VLF), ultra-low (ULF), and high (HF) frequency ranges and for each of said amplitude and heart and/or pulse rate time series of the sensed peripheral pulse signal.

24. The system according to claim 23, wherein said plurality of variables further includes a spectral density peak ratio of LF to HF for at least one of the amplitude and said heart and/or pulse rate time series of the sensed peripheral pulse signal.

25. The system according to claim 23, wherein said plurality of variables further includes a spectral density peak ratio of LF to HF for each of the amplitude and said heart and/or pulse rate time series of the sensed peripheral pulse signal.

26. The system according to claim 25, wherein said plurality of variables further includes a mean of at least one of the amplitude and said heart and/or pulse rate time series of the sensed peripheral pulse signal.

27. The system according to claim 25, wherein said plurality of variables further includes a mean amplitude and mean heart and/or pulse rate time series of the sensed peripheral pulse signal.

28. The system according to claim 27, wherein said plurality of variables further includes a scaling coefficient of a detrended fluctuation analysis (DFA) of at least one of the amplitude and said heart and/or pulse rate time series of the sensed peripheral pulse signal.

29. The system according to claim 27, wherein said plurality of variables further includes scaling coefficients of a detrended fluctuation analysis (DFA) of each of the amplitude and said heart and/or pulse rate time series of the sensed peripheral pulse signal.

30. The system according to claim 29, wherein said weighted combination represents a probability of a non-REM sleep epoch to be a non-REM deep sleep epoch, and is calculated according to the following equation:

$$Y_{est}(n) = \sum_{j=1}^{14} \sum_{k=-10}^{10} W_{jk} * X_j(n+k)$$

where:

$Y(n)$ is a probability of an epoch n to be a non-REM deep sleep epoch;

$X_j(n)$ is a value of each one of the plurality of filtered variables, said plurality of filtered variables includes 14 variables at epoch n; and $W_{jk}$ are 21 filter coefficients of each epoch k within a sliding window centered around epoch n, said filter coefficients are computed analytically to minimize an error in said determination.

31. The system of claim 17, wherein said plurality of variables includes at least one of the group consisting of:

a spectral density peak ratio of LF to HF for at least one of the amplitude and heart and/or pulse rate time series of the sensed peripheral pulse signal, a mean amplitude or mean heart and/or pulse rate time series of the sensed peripheral pulse signal, and scaling coefficients of a detrended fluctuation analysis (DFA) of at least one of the amplitude and heart and/or pulse rate time series of the sensed peripheral pulse signal.

\* \* \* \* \*